United States Patent [19]
Nikolaychik et al.

[11] Patent Number: 5,660,873
[45] Date of Patent: Aug. 26, 1997

[54] COATING INTRALUMINAL STENTS

[75] Inventors: Victor Nikolaychik, Mequon; Nicholas N. Kipshidze, Bayside; John E. Baker, Wauwatosa, all of Wis.

[73] Assignee: Bioseal, Limited Liability Corporaton, Wauwatosa, Wis.

[21] Appl. No.: 303,866

[22] Filed: Sep. 9, 1994

[51] Int. Cl.$^6$ .................... B05D 3/04; B05D 3/10
[52] U.S. Cl. .............. 427/2.24; 427/2.25; 427/2.31; 427/338; 427/377
[58] Field of Search ............... 427/2.24, 2.31, 427/2.25, 2.1, 2.3, 377, 338, 421, 426; 606/214

[56] References Cited

U.S. PATENT DOCUMENTS

| | | | |
|---|---|---|---|
| 3,523,807 | 8/1970 | Gerendas . | |
| 3,723,244 | 3/1973 | Breillatt, Jr. | 264/311 |
| 4,414,976 | 11/1983 | Schwarz et al. | 128/334 R |
| 4,427,651 | 1/1984 | Stroetmann | 424/46 |
| 4,442,655 | 4/1984 | Stroetmann | 53/428 |
| 4,453,939 | 6/1984 | Zimmerman et al. | 604/368 |
| 4,463,457 | 8/1984 | Kelman | 427/2.24 |
| 4,548,736 | 10/1985 | Müller et al. | 252/315.1 |
| 4,627,879 | 12/1986 | Rose et al. | 106/124 |
| 4,997,425 | 3/1991 | Shioya et al. | 602/43 |
| 5,167,960 | 12/1992 | Ito et al. | 424/423 |
| 5,198,424 | 3/1993 | McEver | 427/2.24 |
| 5,219,328 | 6/1993 | Morse et al. | 606/214 |
| 5,272,074 | 12/1993 | Rubens | 435/180 |
| 5,292,362 | 3/1994 | Bass et al. | 106/124 |
| 5,298,255 | 3/1994 | Sawamoto | 424/423 |
| 5,324,647 | 6/1994 | Rubens et al. | 435/180 |
| 5,437,292 | 8/1995 | Kipshidze et al. | 128/898 |
| 5,464,650 | 11/1995 | Berg et al. | 427/2.3 |
| 5,510,077 | 4/1996 | Dinh et al. | 264/279.1 |
| 5,584,875 | 12/1996 | Duhamel | 427/338 |

OTHER PUBLICATIONS

Flugelman et. al., "Genetically Engineered Endothelial Cells Remain Adherent and Viable After Stent Deployment and Exposure to Flow In Vitro", pp. 348–354, 1992, *Circulation Research*, vol. 70, No. 2, Feb.

George et. al., "Multicenter Investigation of Coronary Stenting to Treat Acute or Threatened Closure After Percutaneous Transluminal Coronary Angioplasty: Clinical and Angiographic Outcomes", pp. 135–143, 1993, *JACC*, vol. 22, No. 1, Jul.

Gordon et. al., "Mechanisms of Restenosis and Redilation Within Coronary Stents—Quantitative Angiographic Assessment", pp. 1166–1174, 1993, *JACC*, vol. 21, No. 5, Apr.

JACC Abstracts, vol. 21, No. 2, Feb., 1993.

Schatz, "A View of Vascular Stents", pp. 445–457, 1989, *Circulation*, vol. 79, No. 2, Feb.

*Primary Examiner*—Diana Dudash
*Attorney, Agent, or Firm*—Sheridan Ross P.C.

[57] ABSTRACT

A method is provided for forming fibrin coatings on a substrate, such as device for implantation in a body. The fibrin coatings are dried to provide a fibrin coating having the ability to be stored for extended periods before use. To provide coatings having high shear force resistance, the substrate is contacted first with thrombin and second with fibrinogen.

27 Claims, 2 Drawing Sheets

COATING INTRALUMINAL STENTS

FIELD OF THE INVENTION

This invention relates generally to fibrin-coated devices for implantation in a body and specifically to fibrin-coated stents.

BACKGROUND OF THE INVENTION

Partial or complete blockage of blood vessels is rapidly becoming a major cause of injury or death. Blood vessel blockages can result in a variety of physical ailments including heart attacks and strokes. Blood vessel blockages may be caused by a variety of agents, including blood clots and the build up of cholesterol on a blood vessel.

Blood vessel blockage is typically treated by bypassing the blocked portion of the blood vessel. The bypass is generally accomplished by using either a graft from a patient's blood vessel or a synthetic conduit.

Alternatively, the blocked portion of the vessel may be reopened or replaced by a vascular stent composed of metal or synthetic materials. In some cases, stents are preferred instead of grafts, because, unlike grafts, stents can be implanted without a surgical procedure. Further, the risks of restenosis (e.g., a narrowing of a blood passageway) is decreased with stents relative to grafts.

The use of stents to reopen or replace the blocked portion of the blood vessel can create complications. Stents can themselves induce partial or complete blocking of the blood vessel by triggering blood clotting in the vicinity of the stent. After implantation, the natural process of fibrin deposition on the stent occurs to initiate the healing process. The deposition of the fibrin in the presence of thrombin triggers platelet activation and the formation of a thrombus or embolus. Bound thrombin can also induce the formation of more fibrin on the stent, thereby narrowing the luminal area of the stent. The reduced luminal area can cause an embolism in the patient.

Several approaches have been employed to overcome the complications associated with vascular stents. In one approach, an anticoagulant is administered to the patient to reduce the likelihood of clotting. Anticoagulants are not widely used because they can cause serious injury or death. In another approach, endothelial cells, the cells lining blood and lymphatic vessels, are seeded onto the stent to facilitate the healing process. The seeding of stents with endothelial cells is also not widely used because seeded stents are difficult, if not impossible, to manufacture. In yet another approach, a fibrin coating is deposited on the stent before implantation to facilitate the healing process. Compared to stents implanted without a fibrin coating, the incorporation of a fibrin coating on an implanted stent reduces significantly the likelihood of blood vessel blockage after implantation.

The approach of forming a fibrin coating on a stent before implantation to reduce or overcome complications has several drawbacks which significantly increase the cost of the fibrin-coated stent. For example, a fibrin coating is unstable outside of the body and generally must be implanted immediately after formation of the coating. A fibrin coating generally does not adhere tightly to the stent and can become dislodged easily from the stent surface. A denatured fibrin coating has been used to enhance adhesion of the coating to the stent surface, but denatured fibrin has a different structure than natured fibrin (e.g., fibrin formed in the body) leading to an increased risk of blood clots. Consequently, denatured fibrin is not as effective as a natured fibrin coating in enhancing healing and reducing the likelihood of blood clotting after implantation.

Accordingly, there is a need for a device to be implanted in a body, such as a stent, having a low risk of inducing blood clot formation after implantation of the device in a body.

There is a further need for an improved method for seeding a device to be implanted in a body with endothelial cells.

There is a further need for a device to be implanted in a body having a fibrin coating that is stable outside the body. There is a related need for a device to be implanted in a body having a fibrin coating that may be stored for long periods before use.

There is a further need for a fibrin coating that has a high degree of adhesion to the surface of the device. There is a related need for a fibrin coating containing a substantial amount of natured fibrin and a limited amount of denatured fibrin.

SUMMARY OF THE INVENTION

One embodiment of the present invention provides a method for forming a fibrin coating on a substrate, particularly on a device for implantation in a body. The method includes the following steps: (i) contacting the substrate with thrombin and fibrinogen to form the fibrin coating on a portion of the substrate and (ii) drying the fibrin coating at a temperature and pressure and for a time sufficient to vaporize a substantial portion of the water in the fibrin coating and thereby cause the coating to adhere to the substrate.

In the contacting step, the substrate can be contacted with thrombin and fibrinogen either separately or together. In the former case, the substrate is preferably contacted with thrombin in the substantial absence of fibrinogen to form a thrombin coating on the substrate and the thrombin-coated substrate is contacted with fibrinogen to form the fibrin coating. In the latter case, the substrate is preferably contacted with a liquid containing both thrombin and fibrinogen.

During contacting, the substrate is preferably contacted with fibrinogen at a temperature of no more than about 56° C. to avoid denaturing of the fibrinogen. More preferably, the substrate is contacted with fibrinogen at a temperature ranging from about 37° to about 56° C.

To provide acceptable rates of fibrin formation, the contacting step is preferably conducted in an atmosphere having a humidity of no less than about 90%.

During the drying step, the temperature and time are preferably selected to cause the removal of water from the fibrin coating. Preferably, the temperature ranges from about 37° to about 65° C. and the time from about 2 to about 24 hrs. After drying, the thickness of the fibrin coating is less than the thickness of the fibrin coating before drying.

After drying, the fibrin coating can be contacted with water, salts and/or a suitable additive for implantation of the substrate into a living body. After contacting the coating with water, salts and/or a suitable additive and before implantation, the fibrin coating can be seeded with living cells to reduce the thrombogenicity of the coating.

Another embodiment of the present invention provides a device for implantation in a living body. The device includes a structural member, such as a prosthetic device, having a fibrin coating on a surface of the member. As used herein, "prosthetic device" shall refer to a substitute for a diseased or missing body part. The water content of the fibrin coating is reduced to no more than about 8% by weight water to increase the useful life of the device before implantation.

The coating can include various additives. The additives include a substance selected from a group consisting of blood clotting inhibitors, anti-inflammatory drugs, smooth muscle cell growth inhibitors, endothelial cell stimulators, antineoplastic reagents, antibiotics, genetic material, and mixtures thereof. As used herein, "anti-inflammatory drug" refers to a substance that reduces inflammation by acting on body mechanisms, without directly antagonizing the causative agent. "Stimulator of endothelial cell growth" refers to a protein that stimulates the growth and/or attachment of endothelial cells and/or chemotaxis. "Antineoplastic reagent" refers to any substance preventing the development, maturation, or spread of neoplastic cells. "Antibiotic" refers to a soluble substance derived either naturally from a mold or bacteria or synthetically that inhibits the growth of microorganisms.

The coating preferably has certain properties. No more than about 19% by weight of the fibrin in the coating should be denatured. The coating should have a thrombogenicity of no more than about 115% of the thrombogenicity of a normal blood vessel wall. The thrombogenicity measures the ability of the coating to trigger clotting of blood contacting the coating. The coating should have a thickness ranging from about 10 to about 200 microns.

Yet another embodiment of the present invention provides another method for forming a fibrin coating on a substrate. The method includes the following steps: (i) contacting the substrate with thrombin in the substantial absence of fibrinogen and (ii) contacting the substrate with fibrinogen to form a fibrin coating on a portion of the substrate. The method can further include a drying step at a temperature and pressure and for a time sufficient to vaporize a substantial portion of the water in the fibrin coating.

The present invention has several advantages over existing substrates to be implanted in a living body. The incorporation of a fibrin coating on substrates of the present invention creates a low risk of blood clot formation after implantation of the substrate. The fibrin coatings of the present invention further provide a suitable environment for seeding the substrate with endothelial cells to reduce the thrombogenicity of the substrate. Fibrin coatings of the present invention can be stable outside the body and stored for extended periods before use. Fibrin coatings of the present invention can be deposited on an unpolished substrate which forms stronger coatings than coatings deposited on a polished substrate. The irregular topography of the unpolished substrate allows a greater contact area for fibrin attachment and limits movement of the fibrin coating. Fibrin coatings of the present invention can be sterilized without complete protein denaturation because drying temperatures are typically below the denaturing temperature. The drying step beneficially kills many viruses not killed by fibrin deposition processes which have no drying step. Fibrin coatings of the present invention can have a high degree of adhesion to the substrate surface and high shear stress resistivity to blood flow. This advantage is especially useful to resist the high shear forces encountered in intravascular applications. Finally, the fibrin coatings of the present invention can contain a substantial amount of natured fibrin and a limited amount of denatured fibrin. The presence of natured fibrin in the coating reduces the thrombogenicity of the coating.

DETAILED DESCRIPTION

Figure 1:
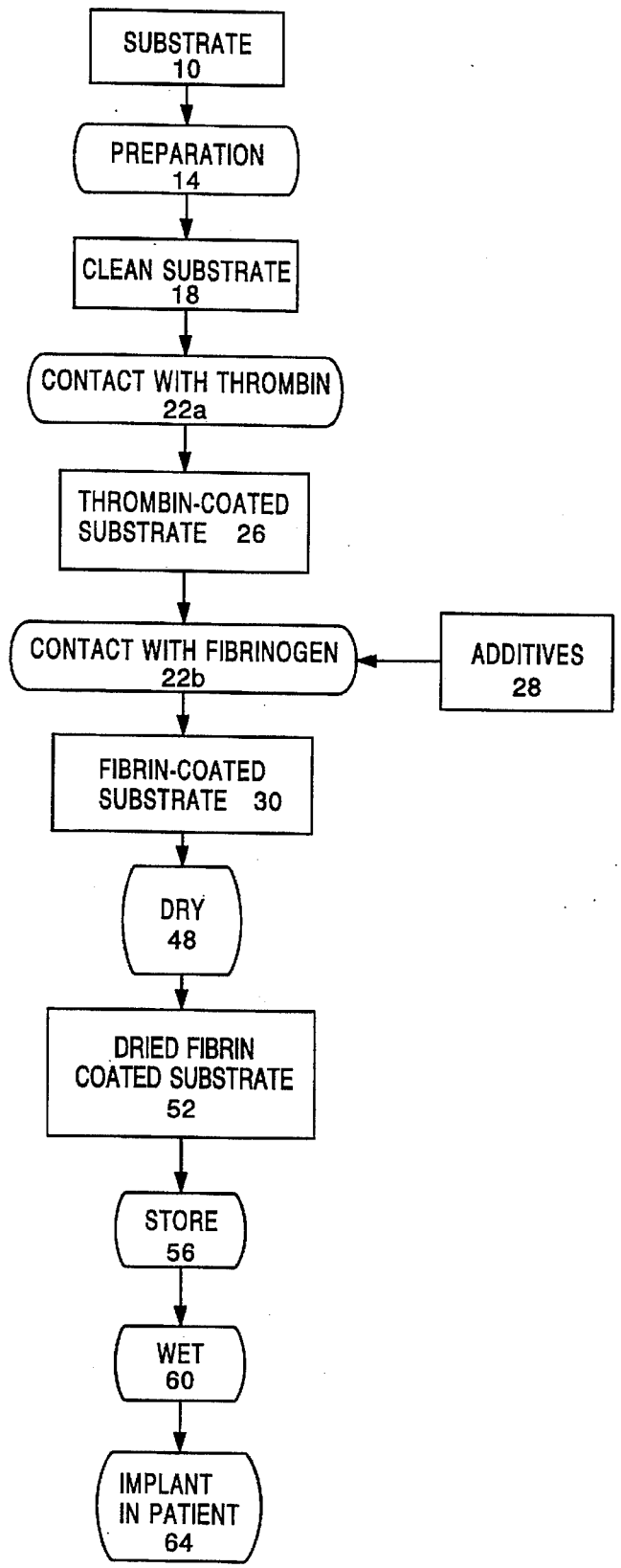
FIG. 1 is a flow chart of a process according to the present invention.

The present invention provides a method for coating a surface of a substrate with fibrin. An important aspect of the invention is the use of a drying step after formation of the fibrin coating to remove water from the coating. The drying step causes the coating to adhere to the substrate and provides a coating that may be stored for extended periods before use. Another important aspect of the invention is the application of thrombin to the substrate followed by contact of the thrombin with fibrinogen to form fibrin. This process produces fibrin coatings having a high degree of adhesion to the substrate surface.

The substrate can be composed of any material that is safe for use in a living body. Preferably, the substrate is composed of a polymeric material, such as poly(ethylene terephthlate), polyethylene, polyurethane, poly(lactic acid), poly(glycolic acid), or poly(tetrafluoroethylene); a metal, such as stainless steel titanium, nitinol, and other alloys; or composites of a polymeric material and a metal. The substrate is preferably a prosthetic device, such as a stent, an artificial heart valve, a cardiac-assist device, or the surfaces of an artificial heart. The substrate can also be a nonprosthetic device, such as a breast implant, pacemaker, or the wires to a pacemaker.

The substrate is contacted with thrombin and fibrinogen to form a fibrin coating on a portion of the substrate. While not wishing to be bound by any theory, it is believed that the fibrin is formed by the action of the thrombin on the fibrinogen. It is believed that the thrombin hydrolyzes peptide bonds in the fibrinogen, which converts fibrinogen to fibrin monomers. The fibrin monomers polymerize to form long-chain polymers which interlock to form a jelly-like mass.

To form the fibrin coating on the substrate, the substrate is preferably contacted first with thrombin in the substantial absence of fibrinogen and second with fibrinogen in the substantial absence of thrombin. As noted above, it has been discovered that contacting the substrate with thrombin before fibrinogen results in a fibrin coating that strongly adheres to the substrate surface. While not wishing to be bound by any theory, it is believed that the presence of thrombin on the substrate surface causes the fibrinogen to form fibrin immediately upon contact with the surface. The direct formation of fibrin on the surface is believed to cause the fibrin monomers to attach directly to the surface.

The thrombin and fibrinogen are preferably contacted with the substrate as separate liquids. A first liquid contains the thrombin, and a second liquid contains the fibrinogen. The first and second liquids are preferably aqueous solutions having a pH ranging from about 6.8 to about 7.8.

The concentrations of the thrombin and fibrinogen in the first and second liquids determine the thickness of the fibrin coating. In the first liquid, the concentration of the thrombin should range from about 0.001 to about 1000 IU/ml, more preferably from about 0.05 to about 500 IU/ml, and most preferably from about 0.1 to about 100 IU/ml. The first liquid is substantially free of fibrinogen, preferably having a concentration of fibrinogen that is no more than about 15 ng/ml. In the second liquid, the concentration of the fibrinogen should range from about 5 to about 75 mg/ml, more preferably from about 5 to about 50 mg/ml, and most preferably from about 10 to about 30 mg/ml. The second liquid is preferably substantially free of thrombin, preferably having a concentration of thrombin that is no more than about 0.0001 IU/ml.

The first and second liquids can contain a stabilizing salt to solubilize the thrombin and/or fibrinogen in the liquids. The stabilizing salt can be any salt, including sodium chloride, magnesium sulfate, sodium sulfate, potassium chloride, calcium chloride, and mixtures thereof. Preferably, the salt concentration in the solution ranges from about 50 to about 300 moles/liter.

The second liquid can contain other additives to impact the properties of the fibrin coating and the reaction of the body to the coating after implantation. The additive can be contacted with the second liquid either as is or as a part of a time-release microcapsule. The time-release microcapsule is typically used where the additive is a medication that is to be released gradually into the body over time.

One additive is a stabilizing agent to stabilize the fibrin coating. While not wishing to be bound by any theory, it is believed that the stabilizing agent catalyzes cross-linking of the fibrin polymers. The cross-linking stabilizes the deposited fibrin, making it resistant to the high fluid shear rates to which intravascular prosthetic devices, such as stents, are subjected. Stabilizing agents include Factor XIII, calcium salts that are soluble in the second liquid (e.g., calcium chloride), and derivatives and mixtures thereof. Preferably, the Factor XIII has a concentration in the second liquid ranging from about 5 to about 500 IU/ml, and the calcium salt a concentration ranging from about 0.1 to about 15 mg/dl.

Another additive is a blood clotting inhibitor (e.g., anticoagulant) to inhibit the formation of blood clots after implantation of the substrate. Preferred blood clotting inhibitors include recombinant hirudin, hirulog-1, D-phenylalanyl-L-prolyl-L-arginyl chloromethyl ketone, heparin and its fractions, dipyridamole, RGD-like peptide, and derivatives and mixtures thereof. The blood clotting inhibitors are generally used at pharmacological concentrations to prevent clotting. The blood clotting inhibitor heparin preferably has a concentration in the second liquid ranging from about 10 to about 500 IU/ml, preferably about 50 to about 250 IU/ml, and more preferably from about 75 to about 150 IU/ml. Dipyridamole preferably has a concentration ranging from about 10 to about 100 moles/ml.

Yet another additive is an anti-inflammatory drug to suppress inflammation of tissue after implantation of the substrate. Anti-inflammatory drugs preferably include antihistamines, glucocorticoids, non-steroidals, salicylates, steroids, and derivatives and mixtures thereof. The anti-inflammatory drug is generally used in the second liquid at pharmacological concentrations.

Yet another additive is an inhibitor of smooth muscle cell growth. In intravascular applications, smooth muscle cells in the blood vessel wall can grow into the blood vessel. The constriction of the luminal area of the blood vessel can cause partial or complete blockage of the blood vessel. Inhibitors of smooth muscle cell growth retard the formation of such constrictions. Preferred inhibitors include nitric oxide donors such as nitrosoglutathione, substrates for nitric oxide production such as L-arginine, and derivatives and mixtures thereof. The inhibitor is generally used in the second liquid at pharmacological concentrations. Specifically, the concentration of L-arginine ranges from about 0.1 to about 5.0 µM and nitrosoglutathione from about 0.1 to about 50 µM.

Yet another additive is a stimulator of endothelial cell growth. In intravascular applications, endothelial cells coat the interior of the blood vessel to separate the blood from the underlying smooth muscles of the blood vessel wall. The contact of the blood with the smooth muscles can cause rapid reproduction of the smooth muscle cells and constriction of the luminal area of the vessel. Preferred stimulators of endothelial cell growth include basic fibroblast cell growth factor, endothelial cell growth factor, $\alpha_2$ macroglobulin, vitronectin, fibronectin, fibronectin fragments containing binding determinants for endothelial cells, and derivatives and mixtures thereof. The stimulator is generally used at pharmacological concentrations. Specifically, fibronectin preferably has a concentration in the second liquid ranging from about 5 to about 150 ng/ml.

Yet another additive is an antineoplastic reagent. Antineoplastic reagents are particularly useful for substrates contacting a cancerous cell growth to inhibit cell proliferation in the growth. Preferred antineoplastic reagents include doxorubicin, taxol, methotrexate, and derivatives and mixtures thereof. The antineoplastic reagent is generally used at pharmacological concentrations. Specifically, doxorubicin preferably has a concentration in the second liquid ranging from about 0.1 to about 1.0 mg/ml.

Yet another additive is an antibiotic. Antibiotics are used to prevent infection after implantation of the substrate. Preferred antibiotics include all broad and medium spectrum agents, including aminoglycolides, cephalosporons (1st, 2nd, and 3rd generation), macrolides, penicillins, tetracyclines, and derivatives and mixtures thereof. The antibiotic is generally used at pharmacological concentrations. Specifically, tobramycin preferably has a concentration in the second liquid ranging from about 10 to about 50 mg/ml.

As will be appreciated, other additives can be incorporated in the second liquid depending upon the desired properties of the coating or the desired effect of the coating on the patient. For example, genetic material may be incorporated with endothelial cells in the second liquid to assist in nitric oxide production by the substrate.

To form the fibrin coating, the substrate can be immersed sequentially in the first and second liquids. Immersing the substrate in the first liquid forms a liquid coating of thrombin on the substrate. The thrombin coating forms fibrin when the substrate is contacted with the second liquid containing fibrinogen.

During immersion of the substrate in the first liquid, the temperature of the liquid preferably ranges from about 21° to about 37° C., and the time of immersion preferably ranges from about 2 to about 24 hrs.

During immersion of the substrate in the second liquid, the temperature of the liquid is preferably maintained below the temperature at which denaturing of the fibrinogen occurs. In human fibrinogen, denaturing typically occurs at temperatures of 56° C. or more. As noted above, denatured fibrinogen forms a fibrin coating having a higher thrombogenicity than a fibrin coating formed from natured fibrin. Preferably, the temperature ranges from about 37° to about 56° C.

It is most preferred that the temperature of the second liquid be maintained as closely as possible at the temperature of the body in which the substrate is to be implanted (e.g., 37° C. for humans) to reproduce as closely as possible the conditions of fibrin formation in the body. Such a temperature favors the formation of a fibrin coating having properties that closely resemble those of a fibrin coating formed in the body.

The time of immersion of the substrate in the second liquid determines the thickness of the fibrin coating. Preferably, the thickness of the fibrin coating after immersion ranges from about 400 to about 5,000 microns. To obtain this thickness, the time of immersion preferably ranges from about 4 to about 20 hrs.

The humidity of the ambient atmosphere is another important factor to fibrin formation. It has been discovered that the humidity of the atmosphere contacting the surface of the second liquid is directly related to the rate of conversion of fibrinogen into fibrin. Preferably, the humidity of the atmosphere is no less than about 90%, more preferably no less than about 92%, and most preferably no less than about 96%.

There are other methods to contact the substrate with thrombin and fibrinogen. Thrombin and fibrinogen also can be contacted with the substrate by spraying the first and/or second liquids on the substrate. As will be appreciated, the thrombin and fibrinogen can also be contacted with the substrate by a combination of immersion and spraying of the first and/or second liquids. Immersion of the substrate in both of the first and second liquids is preferred because this creates greater surface contact area, greater coating flexibility, and a more uniform coating.

Alternatively, the fibrin coating can be formed by contacting the substrate with a single liquid containing both thrombin and fibrinogen. This approach has the advantage of using only one liquid, rather than two liquids, in the formation of the fibrin coating; however, the use of two liquids as described above is believed to form a fibrin coating that adheres to the substrate more strongly than a fibrin coating formed from a single liquid containing both thrombin and fibrinogen.

As yet another alternative, the thrombin and fibrinogen can be applied to the substrate as a solid rather than as a liquid. However for purposes of simplicity and cost, it is preferred to apply thrombin and fibrinogen to the substrate as a liquid.

After formation of the fibrin coating, the coating can be dried at a temperature and pressure and for a time sufficient to vaporize a substantial portion of the water in the fibrin coating and thereby cause the coating to adhere to the substrate. After formation, the fibrin coating has a water content ranging from about 80 to about 96% by weight. As noted above, it is believed that removal of water from the fibrin coating has several advantages, including the ability to store the fibrin coating for extended periods before use and increased adhesion of the coating to the substrate surface. While not wishing to be bound by any theory, it is believed that water acts as a lubricant between the fibrin coating and the substrate and that the water increases the thickness of the coating and decreases the ability of the fibrin polymers to contact one another. In each case, the net result is a decrease in the adhesive forces between the coating and the substrate and the shear strength of the coating. Removal of the water increases the adhesive forces and the shear strength of the coating.

The temperature of the coating during drying is below the melting point of the substrate. Preferably, the coating temperature ranges from about 37° to about 65° C., more preferably from about 45° to about 52° C., and most preferably from about 50° C. to about 51° C.

The pressure during drying is preferably maintained at about atmospheric pressure. The use of higher or lower pressures can significantly increase the cost of the drying equipment.

The time of drying is selected to remove a substantial portion of the water from the coating while suppressing denaturing of the fibrin for drying temperatures in excess of the temperature at which denaturing occurs. Preferably, the time is selected such that drying reduces the water content of the coating to no more than about 8% by weight, more preferably no more than about 5% by weight, and most preferably no more than about 3% by weight. Preferably, the time is also selected such that no more than about 19% by weight, more preferably no more than about 15% by weight, and most preferably no more than about 13% by weight of the fibrin in the fibrin coating is denatured after drying. Accordingly, the time ranges from about 2 to about 24 hrs, more preferably from about 4 to about 20 hrs, and most preferably from about 6 to about 18 hrs.

The composition of the ambient atmosphere during drying is an important aspect of the drying step. The atmosphere should be sterile and have less than a saturation amount of water vapor to facilitate water removal from the coating. Preferably, the atmosphere is substantially composed of an inert gas, such as nitrogen or argon.

After drying, the thickness of the fibrin coating is reduced and the density of the coating increased. Typically, the thickness of the fibrin coating after drying is no more than about 5% of the thickness of the coating before drying. As a consequence, the thickness of the coating after drying preferably ranges from about 10 to about 200 microns.

After drying, the fibrin coating has a low thrombogenicity compared to conventional fibrin coatings. Preferably, the thrombogenicity of the coating is no more than about 115% of the thrombogenicity of a normal blood vessel wall.

Before implantation of the dried fibrin coating in a body, it is important to add water, salt, and pharmacologic agents to the fibrin coating. Before use, the dried fibrin coating is preferably contacted with water and salts to increase the flexibility and non-thrombogenicity of the coating to acceptable levels for implantation. The moisture content of the dried fibrin coating is preferably increased by immersing the coating in water or exposing the coating to water vapor. Surprisingly, the thickness of the coating after rehydration is less than the coating thickness before drying. Relative to stents, the reduced thickness provides an increased luminal area of a stent.

Following the replenishment of water to the coating, the fibrin coating can be seeded with endothelial cells to further reduce the thrombogenicity of the coating. The stability of the fibrin coating makes it an excellent substrate for endothelial cell seeding. Endothelial cells can be obtained by standard procedures from umbilical vein, saphenous vein, microvessels of fat-containing tissues, or other sources. For seeding, the cells are cultured on the coating in the presence of a culture medium, generally at body temperature in an atmosphere containing carbon dioxide. Satisfactory attachment of the endothelial cells to the fibrin coating is generally realized within about 1 and about 3.5 hrs. After seeding, the fibrin coating is incubated to allow the endothelial cells to reproduce.

Alternatively when the coating is not to be dried before implantation, cultured endothelial cells can be included within the second liquid to trap the cells within the coating. The coating is then incubated as noted above. Drying the coating will kill the endothelial cells.

Smooth muscle cells, fibroblasts and/or derivatives and/or mixtures thereof with endothelial cells may also be included in the second liquid and the fibrin coating.

Referring to FIG. 1, the preferred embodiment of the present invention, the substrate 10 is prepared 14 before formation of the fibrin coating to form a clean substrate 18. Typically, the substrate is cleaned and sterilized by being rinsed with methanol or ethanol to remove contaminants. The methanol or ethanol rinse is followed by a rinse in tris buffered solution ("TBS") or phosphate buffered solution ("PBS"). As necessary, the clean substrate 18 can be stored in TBS or PBS.

The clean substrate 18 is contacted 22a, b with thrombin and fibrinogen to form the fibrin coating. The clean substrate 18 is immersed in a first liquid containing thrombin to form a thrombin-coated substrate 26. The thrombin-coated substrate 26 is immersed in a second liquid containing fibrinogen and one or more of the additives 28 noted above to deposit the fibrinogen on the thrombin-coated substrate 26 and form a fibrin-coated substrate 30.

Figure 2:
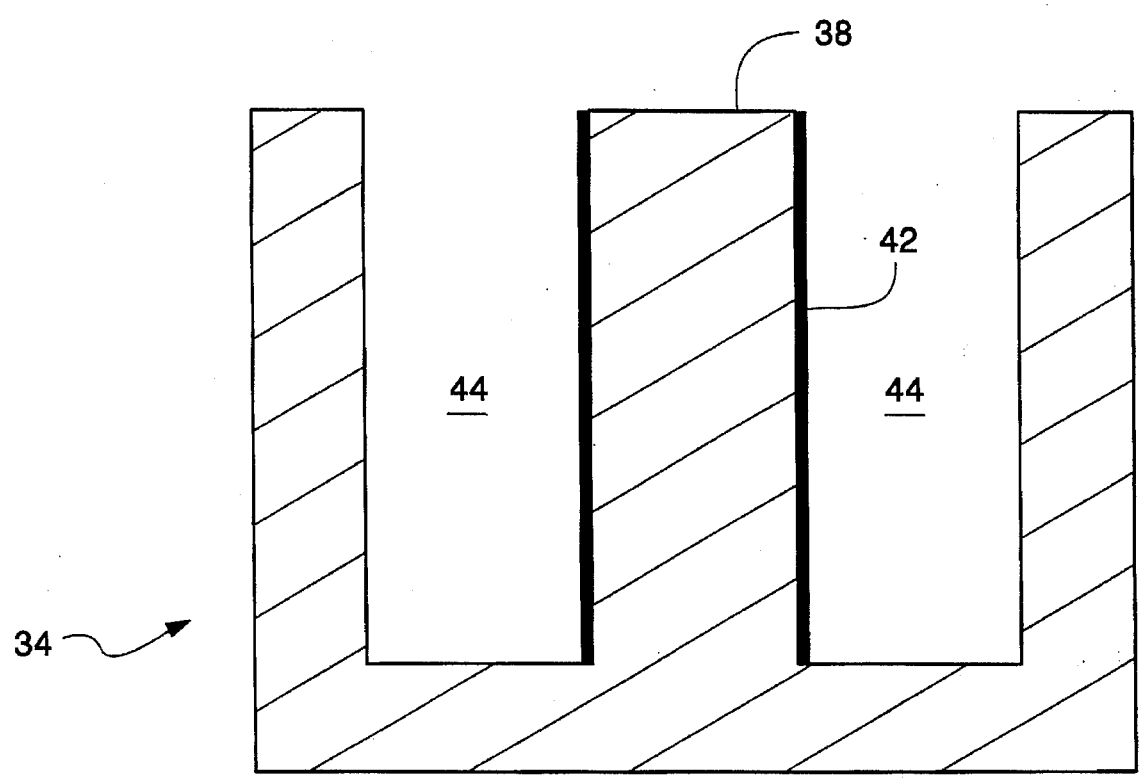
FIG. 2 is a side view of an incubation chamber.

The size and design of the vessel used for fibrin formation depends on the size and shape of clean substrate 18. The preferred vessel design for a stent is depicted in FIG. 2. The vessel 34 includes a cylindrical member 38 that has a size that closely matches the inner diameter of the stent 42. The vessel interior 44 is filled sequentially with the first and second liquids to form the fibrin coating on the stent 42. The vessel 34 can include heating elements (not shown) to maintain the temperature of the first and second liquids at desired levels.

The fibrin-coated substrate is dried 48 to remove water from the fibrin to yield a dried fibrin-coated substrate 52.

Known dryers can be utilized to dry the fibrin coating. The size and shape of the dryer depends upon the size, shape and composition of the substrate.

The dried fibrin-coated substrate 52 is stored 56 under sterile conditions for an extended period and wetted 60 with water, salts and/or the additives noted above for implantation in the patient 64.

EXAMPLES

A series of experiments were conducted to evaluate the effects of drying on the properties of fibrin coatings. During the experiments, the following reagents were used:

| Fibrinogen | 10–30 mg/ml |
| Thrombin | 0.1–100 IU/ml |
| Heparin | 10–500 IU/ml |
| Dipyridamole | 10–100 moles/ml |
| RGD-Like Peptide | 0.1–100 mg/ml |

The fibrinogen, thrombin, and other reagents were combined in an aqueous solution in the presence of a stent at room temperature. The solution was not agitated.

After 2–10 minutes, the stent was transferred to an incubator at 37° C. and 90% humidity for 10–12 hours.

Thereafter, factor XIII was contacted with the solution at 37° C. for approximately 2 hours.

The stent was transferred to an oven for 6–18 hours for drying.

The concentrations of the fibrinogen and thrombin and oven temperatures during the various experiments are set forth below:

| | Reagent | | Drying Oven Temperature |
|---|---|---|---|
| 1. | Fibrinogen | 10 mg/ml | 45° C. |
| | Thrombin | 5 IU/ml | |
| 2. | Fibrinogen | 30 mg/ml | 45° C. |
| | Thrombin | 5 mg/ml | |
| 3. | Fibrinogen | 10 mg/ml | 56° C. |
| | Thrombin | 5 IU/ml | |
| 4. | Fibrinogen | 30 mg/ml | 56° C. |
| | Thrombin | 5 IU/ml | |

After formation, the fibrin coatings were examined under intense light and electron microscopy. The coatings were found to be uniform and substantially free of cracking.

The fibrin-coated stents were then mounted on a balloon and the balloon expanded to replicate the mounting of the stent on a blood vessel. The stent was again examined under intense light and electron microscopy. The fibrin coating was still found to be uniform and substantially free of cracks.

The foregoing description of the invention has been presented for purposes of illustration and description. Further, the description is not intended to limit the invention to the form discussed herein. Consequently, variations and modifications commensurate with the above teachings, and the skill or knowledge in the relevant art are within the scope of the present invention.. The preferred embodiment described hereinabove is further intended to explain the best mode of practicing the invention and to enable others skilled in the art to utilize the invention in various embodiments and with the various modifications required by their particular applications or uses of the invention. It is intended that the appended claims be construed to include alternate embodiments to the extent permitted by the prior art.

What is claimed is:

1. A method for forming a dried fibrin coating on a substrate, comprising the steps of:
   (a) providing the substrate;
   (b) contacting the substrate with water, thrombin and fibrinogen in an atmosphere having a humidity of no less than about 90% to form a coating on at least a portion of the substrate, wherein the coating comprises water and fibrin; and
   (c) heating the coating at a temperature above the freezing point of water for a time sufficient to vaporize the majority of the water in the coating and form a dried fibrin coating containing water, whereby the fibrin in the dried fibrin coating is stabilized.

2. The method, as claimed in claim 1, wherein:
   in said heating step, the coating is in the presence of an atmosphere including less than a saturation amount of water vapor and a gas that is nonreactive with fibrin.

3. The method, as claimed in claim 1, wherein said contacting step comprises:
   first contacting the substrate with thrombin in the substantial absence of fibrinogen to form a thrombin coating on the portion of the substrate; and
   second contacting the substrate with fibrinogen to form the coating.

4. The method, as claimed in claim 1, wherein the contacting step comprises:
   contacting the substrate with an aqueous solution comprising thrombin and fibrinogen.

5. The method, as claimed in claim 1, wherein:
   in said contacting step, the substrate is contacted with a liquid comprising from about 0.001 to about 1000 IU/ml of thrombin.

6. The method, as claimed in claim 1, wherein:

in the contacting step, the substrate is contacted with a liquid comprising from about 5 to about 75 mg/ml fibrinogen.

7. The method, as claimed in claim 1, wherein:

the contacting step is conducted at a temperature below the temperature at which the fibrinogen becomes denatured.

8. The method, as claimed in claim 1, wherein:

in the contacting step, the substrate is contacted with fibrinogen at a second temperature ranging from about 37° to about 56° C. for a time sufficient to induce formation of fibrin in the coating.

9. The method, as claimed in claim 1, wherein:

in the contacting step, the substrate is contacted with a liquid comprising a substance selected from the group consisting of thrombin, fibrinogen, or mixtures thereof; and wherein the contacting step comprises:

spraying the liquid onto the substrate to form the fibrin coating.

10. The method, as claimed in claim 1, wherein:

(a) the substrate is a device for implantation in a body.

11. The method, as claimed in claim 1, wherein the contacting step further comprises:

contacting the coating with a compound selected from the group consisting of Factor XIII, a calcium salt, and mixtures thereof to catalyze cross-linking of the fibrin.

12. The method, as claimed in claim 1, wherein:

no more than about 19% by weight of the fibrin in the dried fibrin coating is denatured.

13. The method, as claimed in claim 1, wherein:

in the contacting step, the substrate is further contacted with a liquid comprising from about 10 to about 100 moles/ml of one of a dipyridamole, an RGD peptide, and mixtures thereof.

14. The method, as claimed in claim 1, wherein:

the temperature ranges from about 37° to about 65° C.

15. The method, as claimed in claim 1, wherein:

the time ranges from about 2 to about 24 hrs.

16. The method as claimed in claim 1, wherein after the heating step the coating comprises no more than about 8% by weight water.

17. A method for forming a dried fibrin coating on a substrate, comprising the steps of:

(a) providing the substrate;

(b) contacting the substrate with water, fibrinogen and thrombin in an atmosphere having a humidity of no less than about 90% to form a coating comprising fibrin and water on at least a portion of the substrate;

(c) maintaining the coating at a temperature of at least about 37° C. to remove a majority of the water from the coating to form a dried fibrin coating containing water whereby the fibrin in the dried fibrin coating is stabilized.

18. The method, as claimed in claim 17, wherein in said drying step:

the thickness of the dried fibrin coating is no more than about 5% of the thickness of the coating before the maintaining step.

19. The method as claimed in claim 17, wherein the contacting step is conducted at a temperature below the temperature at which the fibrinogen becomes denatured.

20. The method as claimed in claim 17, wherein the contacting step is conducted at a temperature ranging from about 37° C. to about 56° C.

21. The method as claimed in claim 17, wherein the maintaining step has a duration ranging from about 2 to about 24 hours.

22. The method as claimed in claim 17, wherein:

before the maintaining step the dried fibrin coating has a thickness, ranging from about 10 to about 200 microns.

23. The method as claimed in claim 17, wherein, after the maintaining step, the coating comprises no more than about 8% by weight water.

24. The method as claimed in claim 17, wherein the temperature is no more than about 65° C.

25. A method for forming a fibrin coating on a substrate, comprising the steps of:

(a) contacting a substrate with water, thrombin and fibrinogen to form a coating on at least a portion of the substrate, wherein the coating comprises water and fibrin; and (b) maintaining the coating at a temperature of at least about 37° C. in an atmosphere including less than a saturation amount of water vapor and a gas that is nonreactive with fibrin to vaporize the majority of the water in the coating and form a dried fibrin coating containing water, wherein the thickness of the dried fibrin coating is no more than about 5% of the thickness of the coating before the maintaining step.

26. A method for forming a dried fibrin coating on a substrate, comprising the steps of:

(a) providing the substrate;

(b) contacting the substrate with water, thrombin and fibrinogen to form a coating on at least a portion of the substrate, wherein the coating comprises water and fibrin;

(c) further contacting the substrate with a liquid comprising from about 10 to about 100M/Ml of one of dipyridamole, an RGD peptide, and mixtures thereof; and (d) heating the coating at a temperature above the freezing point of water for a time sufficient to vaporize a majority of the water in the coating and form a dried fibrin coating containing water, whereby the fibrin in the dried fibrin coating is stabilized.

27. A method for forming a dried fibrin coating on a substrate, comprising the steps of:

(a) providing a substrate;

(b) contacting the substrate with water, fibrinogen, and thrombin to form a coating comprising fibrin and water on at least a portion of the substrate;

(c) maintaining the coating at a temperature of at least about 37° C. to remove a majority of the water from the coating to form a dried fibrin coating containing water, whereby the fibrin in the dried fibrin coating is stabilized and wherein the thickness of the dried fibrin coating is no more than about 5% of the thickness of the coating before the maintaining step.

* * * * *